US012603179B2

(12) United States Patent
Cabral Frias et al.

(10) Patent No.: US 12,603,179 B2
(45) Date of Patent: Apr. 14, 2026

(54) COMPUTER VISION MICRO-SERVICE SEIZURE PREVENTION SYSTEM

(71) Applicant: TOSHIBA GLOBAL COMMERCE SOLUTIONS, INC., Durham, NC (US)

(72) Inventors: Roberto Cabral Frias, Zapopan (MX); David J. Steiner, Durham, NC (US); Fredy Serrano, Tlajomulco de Zúñiga (MX); Carlos Alfredo Banda Montes, Zapopan (MX)

(73) Assignee: TOSHIBA GLOBAL COMMERCE SOLUTIONS, INC., Durham, NC (US)

( * ) Notice: Subject to any disclaimer, the term of this patent is extended or adjusted under 35 U.S.C. 154(b) by 76 days.

(21) Appl. No.: 18/404,807

(22) Filed: Jan. 4, 2024

(65) Prior Publication Data

US 2025/0226090 A1     Jul. 10, 2025

(51) Int. Cl.
G16H 50/20          (2018.01)
A61B 5/00           (2006.01)

(52) U.S. Cl.
CPC .......... G16H 50/20 (2018.01); A61B 5/4094 (2013.01)

(58) Field of Classification Search
None
See application file for complete search history.

(56) References Cited

U.S. PATENT DOCUMENTS

| | | |
|---|---|---|
| 8,165,682 B2 | 4/2012 | Gopalsami et al. |
| 11,219,405 B2 | 1/2022 | Harrer et al. |

| | | | | |
|---|---|---|---|---|
| 2013/0278418 A1* | 10/2013 | Vallaire | ................. | G08B 27/00 |
| | | | | 340/539.13 |
| 2015/0100330 A1* | 4/2015 | Shpits | .................... | G16H 50/80 |
| | | | | 705/2 |
| 2016/0178904 A1* | 6/2016 | Deleeuw | .............. | H04N 13/366 |
| | | | | 345/8 |
| 2018/0085000 A1* | 3/2018 | Weffers-Albu | ...... | A61B 5/7282 |
| 2018/0088669 A1* | 3/2018 | Ramaprakash | .......... | G06T 5/92 |
| 2021/0259621 A1* | 8/2021 | Alves | ................... | A61B 5/4094 |
| 2021/0401355 A1* | 12/2021 | Osorio | ................. | A61B 5/7267 |
| 2022/0157474 A1* | 5/2022 | Gurpur | ................. | G16H 50/30 |

(Continued)

FOREIGN PATENT DOCUMENTS

WO      WO-2016172557 A1 * 10/2016  ........... A61B 5/0022

OTHER PUBLICATIONS

Tripathi et al., Detection of Flashy Segment in YouTube Videos using Computer Vision Technique to Prevent Seizure in Epilepsy Patients, 2023 8th International Conference on Communication and Electronics Systems (ICCES), Coimbatore, India, 2023, pp. 1544-1548. (Year: 2023).*

(Continued)

*Primary Examiner* — Anne-Marie K Alderson
(74) *Attorney, Agent, or Firm* — Patterson + Sheridan, LLP; Gero G. McClellan

(57)          ABSTRACT

Methods and apparatus for preventing seizure activity in an environment using a computer vision system deployed within the environment are described. One example method includes detecting a seizure trigger within the environment via one or more camera devices deployed in the environment. At least one user associated with the environment that is susceptible to the seizure trigger is identified. Information associated with the seizure trigger is transmitted to a computing device associated with the at least one user.

13 Claims, 5 Drawing Sheets

(56) References Cited

U.S. PATENT DOCUMENTS

| | | | | |
|---|---|---|---|---|
| 2022/0304630 A1* | 9/2022 | Karoly | ................. | A61B 5/7267 |
| 2023/0028920 A1* | 1/2023 | Steven | ................. | A61B 5/4094 |
| 2023/0172528 A1 | 6/2023 | Wen | | |
| 2024/0303989 A1* | 9/2024 | Lau | ........................... | G06T 7/55 |
| 2025/0000461 A1* | 1/2025 | Ozilgen | ............... | A61B 5/7282 |

OTHER PUBLICATIONS

Das et al., "Application of IoT in detecting health risks due to flickering artificial lights," 2015 International Conference on Advances in Computing, Communications and Informatics (ICACCI), Kochi, India, 2015, pp. 2331-2334 (Year: 2015).*
Photosensitive Epilepsy Active Mitigation System, Authors et. al.: Disclosed Without Attribution, IP.com No. IPCOM000263542D, IP.com Electronic Publication Date: Sep. 9, 2020 (Year: 2020).*
https://www.soraa.com/learn/science/how-test-ledflicker-home.php.
Sung et al., How to avoid flashing lights and photosensitive videos on TikTok, Mashable, Jun. 15, 2021, https://mashable.com/article/how-to-turn-off-flashing-light-tiktok.

* cited by examiner

<u>300</u>

400

Enter

Detect a seizure trigger within an environment, based on evaluating video captured by one or more camera devices deployed within the environment          405

Determine at least one equipment in the environment associated with the seizure trigger          410

Control the at least one equipment to remove the seizure trigger          415

Exit

COMPUTER VISION MICRO-SERVICE SEIZURE PREVENTION SYSTEM

BACKGROUND

A seizure may be characterized as abnormal or excessive synchronous activity in the brain. Seizure activity in the brain may cause the brain to send electrical signals through the peripheral nervous system activating different muscles of the body. Epilepsy, for example, is a neurological disorder marked by sudden recurrent episodes of sensory disturbance, loss of consciousness, or convulsions, commonly referred to as epileptic seizures.

DETAILED DESCRIPTION

Figure 1A:
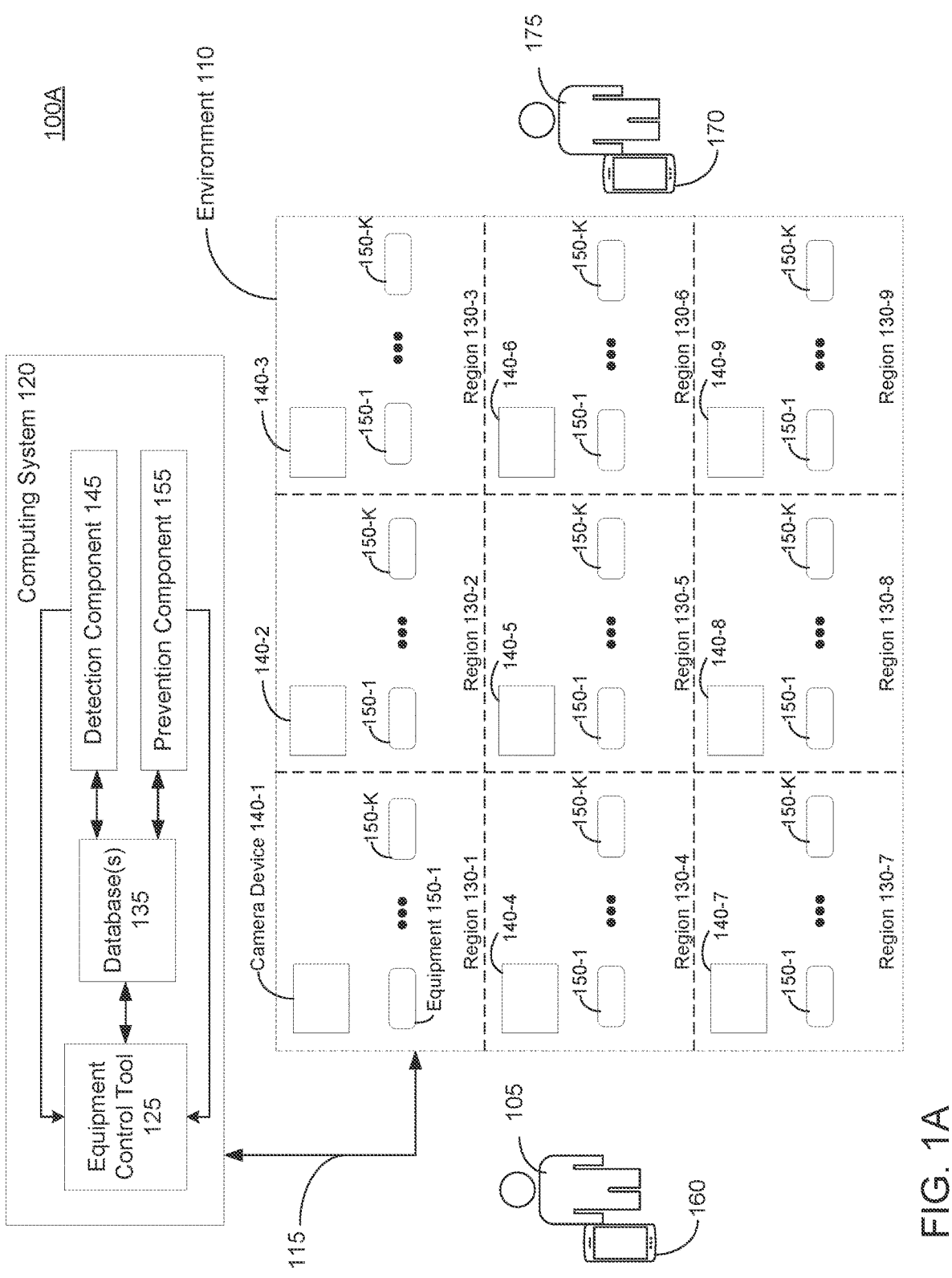
FIG. 1A illustrates an example system, according to one embodiment.

Seizures can be triggered by certain activities, events, environmental phenomena, or a combination thereof. For example, a seizure trigger can be a sight or sound, a substance, or a physiologic state, such as having low blood sugar. Epileptic seizures, for example, can be triggered by stress, lack of sleep, flashing lights or patterns, sounds, illness, and fever, as illustrative, non-limiting examples.

Embodiments described herein provide systems and techniques for preventing seizure activity in an environment equipped with a computer vision (CV) system. For example, environments, such as retail stores, school buildings, stadiums, and other indoor/outdoor environments, may include multiple CV cameras and other sensors deployed throughout the environment. The CV cameras may be used to perform video surveillance, real-time object detection and tracking (e.g., tracking the movement of customers and items in real-time), facial detection, monitor equipment and inventory, or a combination thereof.

In certain embodiments described herein, the CV system within an environment may be configured to monitor for certain seizure triggers (e.g., light patterns) in the environment. For example, individuals with epilepsy may be susceptible to light patterns with certain frequencies and/or color/contrast changes, such as flashing red and/or green lights and high contrast light transitions, as illustrative, non-limiting examples. These light patterns may trigger the onset of seizure activity in sensitive persons, such as individuals with epilepsy. In certain embodiments described in greater detail herein, upon detecting a seizure trigger, the CV system is configured to alert personnel in the environment (e.g., retail store associates) to the existence of the seizure trigger in the environment. Alerting personnel to the presence of seizure triggers may enable the personnel to address the seizure triggers to mitigate the likelihood of such seizure triggers causing seizure activity in sensitive individuals within the environment.

In addition to, or as an alternative to, alerting personnel in the environment, certain embodiments described in greater detail herein may configure the CV system to alert sensitive individuals (e.g., individuals that may be susceptible to certain seizure triggers) to the existence of the seizure trigger in the environment. For example, the CV system may generate and transmit a message to a computing device associated with the sensitive individual that a seizure trigger is present within the environment. Alerting sensitive individuals to the presence of seizure triggers in this manner may enable such individuals to avoid the seizure triggers thereby reducing the likelihood of such seizure triggers causing seizure activity in the sensitive individuals.

In addition to, or as an alternative to, providing alerts to personnel in the environment and/or sensitive individuals as to the existence of seizure triggers in the environment, in certain embodiments described in greater detail herein, the CV system may be configured to control the behavior of one or more electronic equipment in the environment in order to remove the seizure trigger. For example, assuming the seizure trigger is a particular light pattern being displayed on a television within the environment, the CV system may control the television to remove the light pattern (e.g., turn off the television, display a static image, display a different light pattern, etc.).

In certain embodiments, the CV system may be configured to detect when a sensitive individual enters the environment. For example, the environment may provide an application (e.g., retail store application) that can be downloaded to a computing device and used to interact with environment personnel and purchase items in the environment, as illustrative, non-limiting examples. In such an example, a sensitive individual may provide information (e.g., within a user profile) that indicates that the individual is susceptible to certain seizure triggers. In another example, the sensitive individual may interact with personnel within the environment (e.g., at a customer service desk) and provide information to the personnel regarding the individual's susceptibility to certain seizure triggers. After detecting that the sensitive individual is in proximity to the environment, the CV system may perform various actions described herein (e.g., generating alerts, controlling electronic equipment, etc.) to mitigate the likelihood of the seizure trigger causing seizure activity in the sensitive individual.

Additionally, in certain embodiments described in greater detail herein, the CV system may monitor and track the movement of a sensitive individual within the environment. When the CV system detects that the individual is in proximity (e.g., within a threshold distance) to an area within the environment with a seizure trigger, the CV system may perform various actions described herein (e.g., generating alerts, controlling electronic equipment, etc.) to mitigate the likelihood of the seizure trigger causing seizure activity in the sensitive individual. As a reference example, assuming the environment is a retail store and flashing lights are detected in a particular aisle of the retail store, the CV system may turn off the lights in the aisle when the individual approaches that aisle. After the individual moves away from the aisle, the CV system may turn the lights back on in the aisle.

Advantageously, embodiments described herein enable a CV system within an environment to automatically detect seizure triggers within the environment and proactivity perform certain actions to minimize the likelihood of those seizure triggers causing seizure activity in sensitive individuals within the environment.

As used herein, a hyphenated form of a reference numeral refers to an instance of an element and the un-hyphenated form of the reference numeral refers to the collective element. Thus, for example, device "12-1" refers to an instance of a device class, which may be referred to collectively as devices "12" and any one of which may be referred to generically as a device "12."

Note, the techniques described herein for detecting and preventing seizure triggers within an environment may be incorporated into (such as implemented within or performed by) a variety of wired or wireless apparatuses. In some implementations, an apparatus may provide connectivity to or for a network (such as a wide area network (WAN) such as the Internet or a cellular network) via a wired or wireless communication link. In some implementations, an apparatus may include a camera device, a controller (or computing system), or a combination thereof.

FIG. 1A illustrates an example system 100A in which one or more techniques described herein can be implemented, according to one embodiment. As shown, the system 100A includes a computing system 120 that is configured to interact with one or more camera devices 140-1 to 140-9 and one or more equipment 150 deployed within an environment 110. The computing system 120 may be communicatively coupled to the camera devices 140 and equipment(s) 150 via communication link(s) 115, which is generally representative of wireless link(s), wired link(s), or a combination thereof. The environment 110 is generally representative of any geographic area in which one or more camera devices 140 can be deployed. For example, the environment 110 can include an indoor environment, such as a retail store (e.g., grocery store, clothing store, electronic store, etc.), school, or business, as illustrative, non-limiting examples. In another example, the environment 110 can include an outdoor environment, such as a stadium or park, as illustrative, non-limiting examples.

The camera devices 140 are generally representative of a variety of types of electronic camera devices, including, for example, surveillance cameras (e.g., closed-circuit television (CCTV) cameras, digital cameras, RGB cameras, three-dimensional (3D) (or depth) cameras, etc.). Each camera device 140 may include, without limitation, a network interface for communicating with other computers and/or components in the system 100A, an image sensor(s), and imaging optic(s), for example. In certain embodiments, the camera devices 140 may be deployed within the environment 110, such that a substantial portion (or all) of the environment can be monitored with video. By covering a substantial portion of the environment with one or more camera devices, the computing system 120 may be able to perform surveillance monitoring, object detection and tracking, and facial detection of users within the environment 110, as illustrative, non-limiting examples.

Here, for example, the environment 110 includes 9 camera devices 140-1 to 140-9, each deployed in a different region 130 (or area) of the environment 110. In this example, each camera device 140 may have a field of view of the respective region 130 in which the camera device 140 is deployed and may capture video from within its field of view. Note that while FIG. 1A depicts a certain number of camera devices deployed within an environment 110 with a certain number of regions, in other embodiments, a given environment can have any number of camera devices deployed therein as well as any number of regions within the environment. That is, the techniques described herein can be implemented using any number of camera devices deployed within a given environment.

As also shown, the environment 110 includes one or more equipment 150 deployed within the environment 110. Each equipment 150 is generally representative of an electronic device, including but not limited to, televisions, displays, machines (e.g., floor cleaners, fork lifts, etc.), point-of-sale (POS) equipment, etc. Each equipment 150 may include one or more lighting devices (e.g., light-emitting diodes (LEDs)) that provide illumination and/or content (e.g., information, advertising, graphics, etc.). Note that while FIG. 1A depicts a certain number of equipment 150 within each region 130 of the environment 110, in general, each region of a given environment may include any number of equipment of the same type, different type, or combination of types.

In some cases, one or more of the equipment 150 may cause a seizure trigger to a sensitive individual that views, senses, or is otherwise impacted by the seizure trigger. For example, a lighting device(s) associated with the equipment 150 may flash a certain light pattern (e.g., red and/or green, high contrast light transitions) that can cause the onset of seizure activity in a sensitive person. In some cases, the seizure trigger may be caused by equipment failure. For example, a light failure/malfunction may cause the light to flicker in a particular pattern associated with a seizure trigger. In other cases, the seizure trigger may be caused by content being displayed. For example, a television or other display may show advertising or graphics with a light pattern associated with a seizure trigger.

To mitigate the likelihood of seizure triggers within the environment causing seizure activity in sensitive individuals, the computing system 120 described herein is configured to monitor for certain seizure triggers that occur within the environment via the camera devices 140 and, after detecting a seizure trigger, perform one or more actions to reduce the likelihood of that seizure trigger causing seizure activity in a sensitive individual. As shown, the computing system 120 includes an equipment control tool 125, one or more databases 135, a detection component 145, and a prevention component 155, each of which can include hardware, software, or a combination thereof. In certain embodiments, the equipment control tool 125, the database(s) 135, the detection component 145, the prevention component 155, or a combination thereof, may be implemented using a microservices architecture.

The equipment control tool 125 is generally configured to control operation of the equipment(s) 150 in the environment 110. For example, the equipment control tool 125 may be communicatively coupled to the equipment(s) 150 via communication link(s) 115, which can include wireless links, wired links, or a combination thereof. In certain embodiments, the equipment control tool 125 can control one or more lighting devices associated with the equipment 150. For example, the equipment control tool 125 can perform on/off operation for the lighting devices, control/modify the light pattern(s) emitted by the lighting devices, or a combination thereof.

The detection component 145 is generally configured to monitor the environment 110 via the camera devices 140 for the presence of one or more seizure triggers. For example, the detection component 145 may receive video from each of the camera devices 140-1 to 140-9 deployed in the environment 110. The detection component 145 may analyze the video the camera devices 140-1 to 140-9 using a variety of computer vision algorithms and/or machine learning models that are configured to detect certain seizure triggers. In one particular embodiment, the detection component 145 can analyze video from the camera devices 140 for triggers associated with epileptic seizures. Such triggers, for example, can include flashing red and/or green and/or high contrast light transitions.

The detection component 145 may store information associated with detected seizure triggers in the database(s) 135. Such information can include, for example, a location of the seizure trigger in the environment 110, a type of the seizure trigger, or a combination thereof. Note while FIG. 1A depicts database(s) 135 within the computing system 120, in certain embodiments, the database(s) 135 may be located external to the computing system 120. The database(s) 135 may be located in a cloud computing environment or located on-premises (e.g., in the environment 110). Similarly, while FIG. 1A depicts the detection component 145, the prevention component 155, and the equipment control tool 125 as separate components, in certain embodiments, the detection component 145, the prevention component 155, and the equipment control tool 125 may be implemented using a single component (or in general, with any number of components).

The prevention component 155 is generally configured to perform one or more actions to prevent the likelihood of the detected seizure trigger causing seizure activity in a sensitive individual. In certain embodiments, the prevention component 155 may generate and transmit an indication that a seizure trigger has been detected in the environment. In such embodiments, the indication may be sent to (i) computing device(s) associated with personnel in the environment responsible for managing the environment (e.g., associates, administrators, management, etc.), (ii) computing device(s) associated with sensitive individuals, or (iii) a combination thereof.

In the particular embodiment depicted in FIG. 1A, for example, the user 105 is representative of an individual that is susceptible to certain seizure triggers and the user 175 is representative of personnel associated with the environment 110 (e.g., the user 175 may be an associate or employee responsible for managing the environment 110). In this case, the prevention component 155 may be configured to generate and transmit an alert to the computing device 160 associated with user 105 that at least one seizure trigger has been detected in the environment 110. The alert transmitted to the computing device 160 may include an indication of which region 130 within the environment 110 the seizure trigger was detected, the type of seizure trigger (e.g., type of light pattern detected), or a combination thereof. In an example scenario, assuming the seizure trigger is occurring from a flickering light on a particular aisle (e.g., aisle 5) in a retail environment, the alert transmitted to the computing device 160 may indicate "Avoid aisle 5, light malfunctioning."

In certain embodiments described in greater detail herein, the computing device 160 may host an application associated with the environment 110 that allows the user 105 to interact with personnel in the environment, browse items for purchase, and purchase items, as illustrative, non-limiting examples. In these embodiments, the application may allow the user 105 to provide information that indicates that the user 105 is susceptible to certain types of seizure triggers. In addition, the application may include functionality that allows the computing system 120 to have visibility to the location of the computing device 160 (and, by proxy, the location of the user 105). In such cases, when the computing system 120 determines that the user 105 is within proximity (e.g., within a threshold distance) of the environment 110 or a particular region 130 within the environment in which the seizure trigger is located, the computing system 120 (via the prevention component 155) can transmit the alert to the computing device 160 (and/or trigger the computing device 160 to generate the alert via the application hosted on the computing device 160).

In certain embodiments, the prevention component 155 may be configured to generate and transmit an alert to the computing device 170 associated with user 175 that at least one seizure trigger has been detected in the environment 110. The alert transmitted to the computing device 170 may include an indication of which region 130 within the environment 110 the seizure trigger was detected, the type of seizure trigger (e.g., type of light pattern detected), or a combination thereof. In an example scenario, assuming the seizure trigger is occurring from a flickering light on a particular aisle (e.g., aisle 5) in a retail environment, the alert transmitted to the computing device 170 may indicate "Address malfunctioning light on aisle 5."

In certain embodiments, the computing device 170 may host an application associated with the environment 110 that allows the user 175 to interact with other personnel in the environment and perform one or more management activities, as illustrative, non-limiting examples. In these embodiments, the application may allow the user 175 to view information that indicates whether one or more sensitive individuals are currently present within (or in proximity to) the environment 110, a location(s) of sensitive trigger(s) detected within the environment, and type(s) of sensitive trigger(s) detected within the environment, as illustrative, non-limiting examples. In addition, the application may include functionality that allows the user 175 to register another individual (e.g., user 105) that may be susceptible to seizure triggers with the computing system 120. For example, assuming the computing system 120 does not have an indication that a particular user 105 within the environment 110 is susceptible to seizure triggers, the user 105 may interact with the user 175 and provide information regarding the user's 105 susceptibility to certain seizure triggers. From this point on, the computing system 120 may monitor a position of the user 105 via the computing device 160 and/or via the camera devices 140 to determine whether the user 105 is in proximity to the location of a seizure trigger in the environment 110.

Additionally, in certain embodiments, the application (within computing device 170) may include functionality that allows the user 175 to update a status regarding one or more seizure triggers in the environment 110. For example, the user 175 may be able to indicate whether the seizure trigger has been removed, whether the seizure trigger is still present, etc. In one example scenario, assuming a given seizure trigger has been removed in the environment, the user 175 can use the application on computing device 170 to trigger alerts to the computing device 160 (associated with user 105) that the seizure trigger is no longer present. Additionally or alternatively, such an alert may be triggered after the detection component 145 determines, based on the camera devices 140, that the seizure trigger is no longer present.

In certain embodiments, the prevention component 155 may control one or more equipment 150 in order to remove the seizure trigger that is detected within the environment 110. For example, the prevention component 155 may trigger the equipment control tool 125 to send commands to the equipment 150 associated with the seizure trigger to modify the behavior of the equipment 150. In one example scenario, assuming the seizure trigger is occurring from a television (or a display used for content, such as advertising), the prevention component 155 may trigger the equipment control tool 125 to turn off the television or switch the content being displayed to a non-flashing static image. In another example scenario, assuming the seizure trigger is occurring from a set of lights on a device (e.g., floor cleaner, fork lift, etc.) that are blinking, the prevention component 155 may trigger the equipment control tool 125 to switch the set of lights to blink at a different blink rate or turn blinking off. In yet another example scenario, assuming the seizure trigger is occurring from motion triggered lighting in an apparatus (e.g., refrigerated cabinet), the prevention component 155 may trigger the equipment control tool 125 to switch a trigger mode of the motion triggered lighting (e.g., the lighting the apparatus may be turned on as opposed to being triggered by motion). In a further example scenario, assuming the seizure trigger is occurring from a light that is flickering in an aisle of a retail environment, the prevention component 155 may be configured to turn off the light. In yet another example scenario, assuming the seizure trigger is occurring from a flashing light(s) located on a POS device, the prevention component 155 may be configured to turn the flashing light(s) on the POS device solid (as opposed to flashing) or turn the flashing light(s) on the POS device off.

Figure 1B:
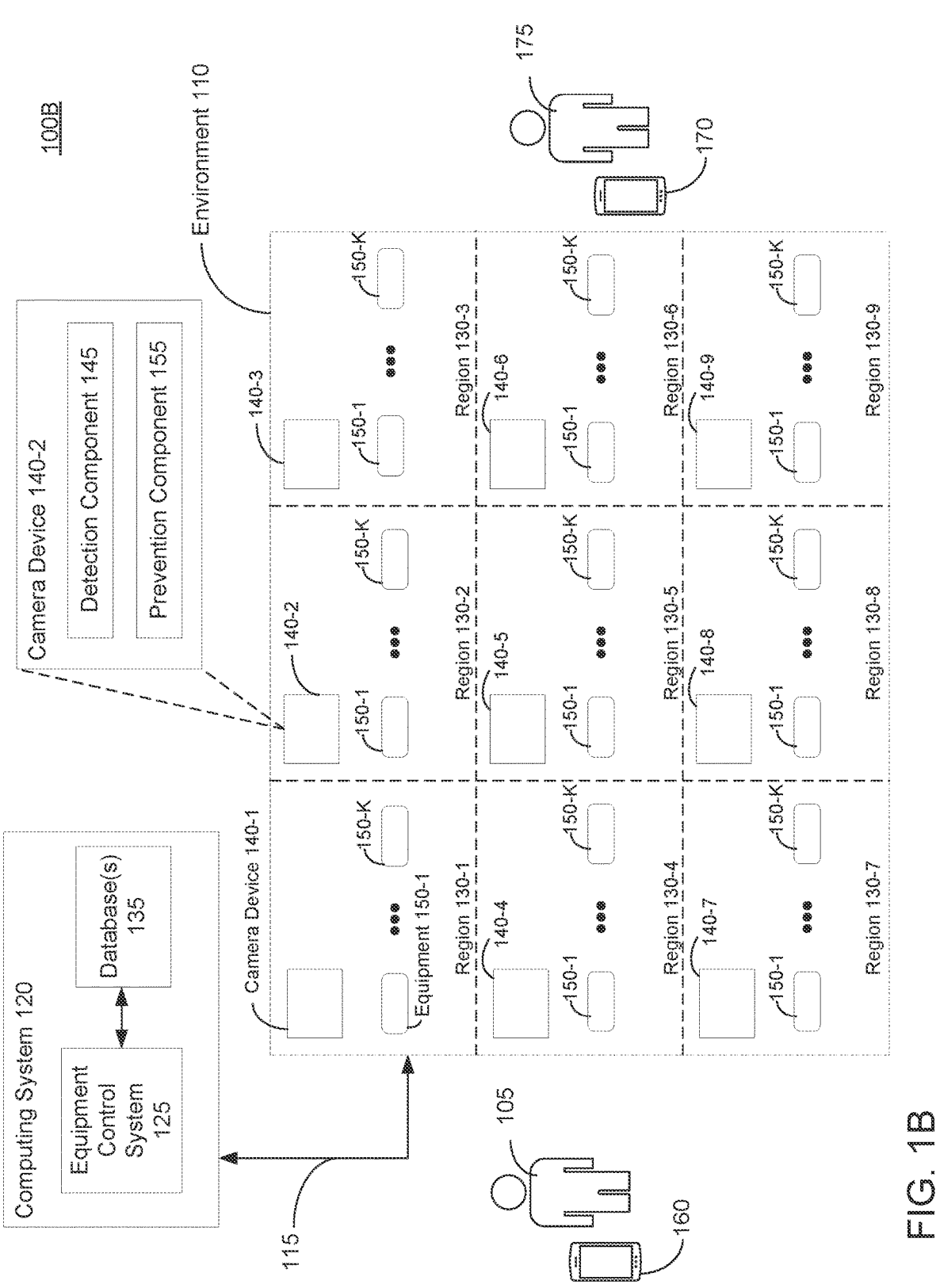
FIG. 1B illustrates an example system, according to one embodiment.

Note that FIG. 1A depicts a reference example configuration of a system in which the techniques presented herein can be implemented and that other system configurations are contemplated. FIG. 1B, for example, illustrates another system 100B in which the techniques presented herein can be implemented. Compared to the system 100A depicted in FIG. 1A, each camera device 140 in the system 100B of FIG. 1B may include a respective detection component 145 and prevention component 155. In this embodiment, the detection component 145 and prevention component 155 may be implemented using a microservices architecture.

Figure 2:
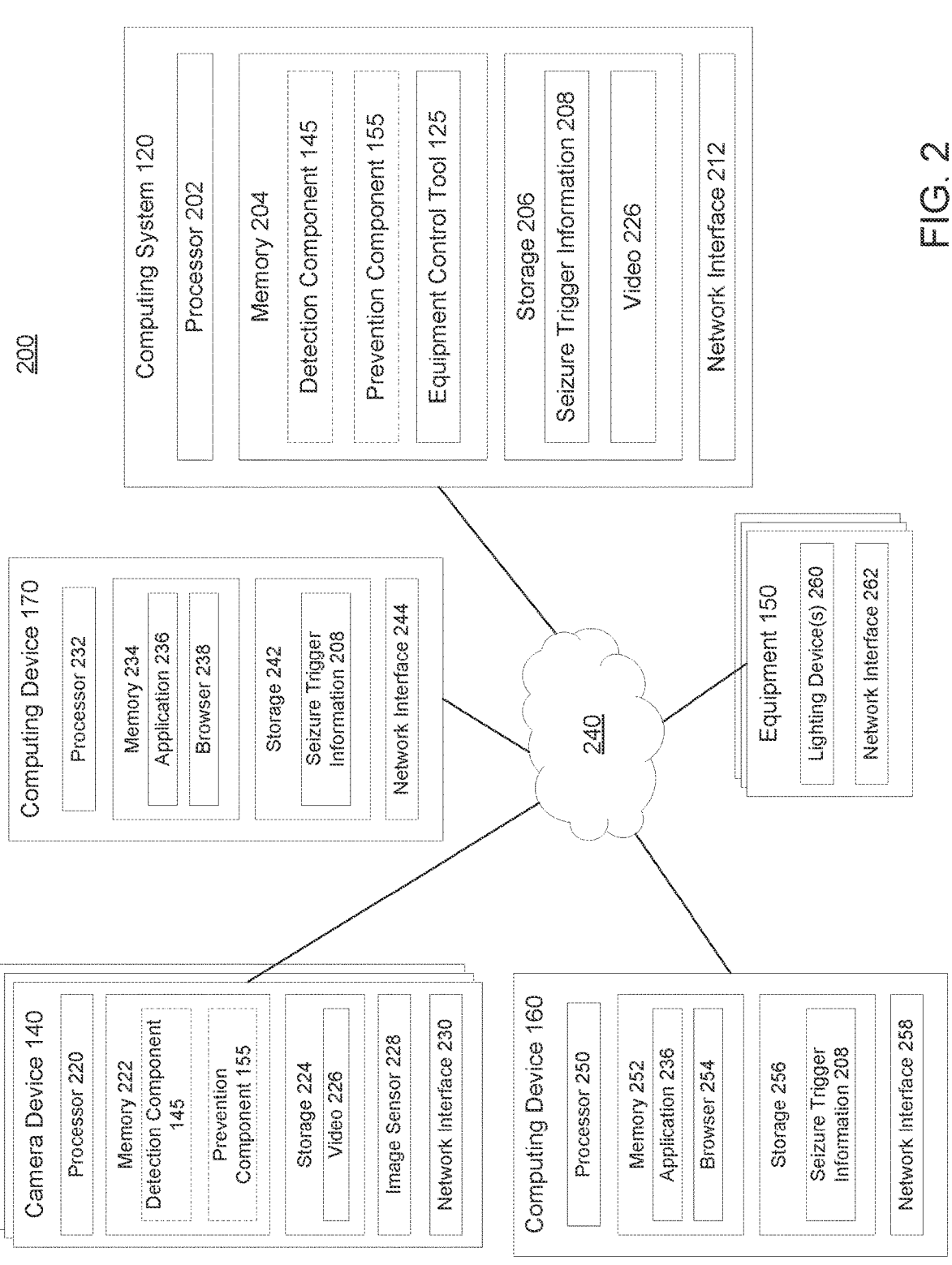
FIG. 2 illustrates an example computing environment, according to one embodiment.

FIG. 2 illustrates an example computing environment 200 in which the techniques described herein can be implemented, according to one embodiment. The computing environment 200 may be used to implement the system 100A depicted in FIG. 1A or the system 100B depicted in FIG. 1B.

As shown, the computing environment 200 includes, without limitation, one or more camera devices 140, one or more equipment 150, a computing device 160, a computing device 170, and a computing system 120, each interconnected via a network 240. The network 240 is generally representative of a local area network (LAN), wide area network (WAN), cellular network, etc.

As noted, the camera device(s) 140 is generally configured to capture video of an area of the environment 110 within a field-of-view of the camera device(s) 140. The camera device(s) 140 includes a processor 220, a memory 222, a storage 224, an image sensor 228, and a network interface 230. The image sensor 228 is representative of a variety of types of electronic image sensors. The network interface 230 may include any communication interface (e.g., serial, wireless, etc.) that allows the camera device 140 to communicate with other computers and/or components in the computing environment 200.

The processor 220 may be any processing element capable of performing the functions described herein. The processor 220 represents a single processor, multiple processors, a processor with multiple cores, and combinations thereof. The memory 222 may be either volatile or non-volatile memory and may include RAM, flash, cache, disk drives, and other computer readable memory storage devices. Although shown as a single entity, the memory 222 may be divided into different memory storage elements such as RAM and one or more hard disk drives. In certain embodiments, the memory 222 includes various instructions that are executable by the processor 220 to perform one or more techniques described herein. Here, the memory 222 may include the detection component 145, the prevention component 155, or a combination thereof.

The storage 224 may be a combination of fixed and/or removable storage devices, such as fixed disc drives, removable memory cards, optical storage, network attached storage (NAS), or a storage area-network (SAN). In certain embodiments, the storage 224 may include video 226, which may include a sequence of images captured by the camera device 140.

Computing device 160 is generally representative of a variety of computing devices, including, for example, a smartphone, a tablet, a laptop computer, etc. Here, the computing device 160 includes a processor 250, memory 252, storage 256, and a network interface 258. The network interface 258 may include any communication interface (e.g., serial, wireless, etc.) that allows the computing device 160 to communicate with other computers and/or components in the computing environment 200.

The processor 250 may be any processing element capable of performing the functions described herein. The processor 250 represents a single processor, multiple processors, a processor with multiple cores, and combinations thereof. The memory 252 may be either volatile or non-volatile memory and may include RAM, flash, cache, disk drives, and other computer readable memory storage devices. Although shown as a single entity, the memory 252 may be divided into different memory storage elements such as RAM and one or more hard disk drives.

In certain embodiments, the memory 252 includes various instructions that are executable by the processor 250 to perform one or more techniques described herein. Here, the memory 222 includes a browser 254 and an application 236, which may include functionality that allows user of the computing device 160 to interact with personnel within a given environment 110, browse/purchase items within the environment 110, and receive alerts and/or information regarding one or more seizure triggers detected within the environment, as illustrative, non-limiting examples.

For example, the browser 254 may be used to access a computing service (e.g., computing system 120) associated with the environment 110 by rendering web pages received from the computing service. Similarly, the application 236 may be representative of a component of a client server application (or other distributed application) that can communicate with the computing service over network 240. Application 236 may be a "thin" client where the processing is largely directed by application, but performed by the computing service, or a conventional software application installed on the computing device. Although not shown, such a computing service within computing system 120 may generally be modeled as a service back end (e.g., web server, application server, and a database). may include the detection component 145, the prevention component 155, or a combination thereof.

The storage 256 may be a combination of fixed and/or removable storage devices, such as fixed disc drives, removable memory cards, optical storage, network attached storage (NAS), or a storage area-network (SAN). In certain embodiments, the storage 256 may include seizure trigger information 208.

Computing device 170 is generally representative of a variety of computing devices, including, for example, a smartphone, a tablet, a laptop computer, etc. Here, the computing device 170 includes a processor 232, memory 234, storage 242, and a network interface 244. The network interface 244 may include any communication interface (e.g., serial, wireless, etc.) that allows the computing device 170 to communicate with other computers and/or components in the computing environment 200.

The processor 232 may be any processing element capable of performing the functions described herein. The processor 232 represents a single processor, multiple processors, a processor with multiple cores, and combinations thereof. The memory 234 may be either volatile or nonvolatile memory and may include RAM, flash, cache, disk drives, and other computer readable memory storage devices. Although shown as a single entity, the memory 234 may be divided into different memory storage elements such as RAM and one or more hard disk drives.

In certain embodiments, the memory 234 includes various instructions that are executable by the processor 232 to perform one or more techniques described herein. Here, the memory 234 includes a browser 238 and application 236, which may include functionality that allows user of the computing device 170 to interact with personnel within a given environment 110, manage the environment 110, and send and/or receive alerts and/or information regarding one or more seizure triggers detected within the environment, as illustrative, non-limiting examples. For example, the browser 238 may be used to access a computing service (e.g., computing system 120) associated with the environment 110 by rendering web pages received from the computing service.

The storage 242 may be a combination of fixed and/or removable storage devices, such as fixed disc drives, removable memory cards, optical storage, network attached storage (NAS), or a storage area-network (SAN). In certain embodiments, the storage 242 may include seizure trigger information 208.

As noted, the equipment(s) 150 is generally representative of an electronic device, including but not limited to, televisions, displays, machines (e.g., floor cleaners, fork lifts, etc.), POS equipment, etc. The equipment(s) 150 may include one or more lighting devices 260 and a network interface 262. The network interface 262 may include any communication interface (e.g., serial, wireless, etc.) that allows the equipment 150 to communicate with other computers and/or components in the computing environment 200. The lighting devices 260 may be configured to provide illumination and/or content. One reference non-limiting example of a lighting device(s) 260 is an LED(s).

The computing system 120 includes a processor 202, a memory 204, a storage 206, and a network interface 212. The network interface 212 may include any communication interface (e.g., serial, wireless, etc.) that allows the computing system 120 to communicate with other computers and/or components in the computing environment 200.

The processor 202 may be any processing element capable of performing the functions described herein. The processor 202 represents a single processor, multiple processors, a processor with multiple cores, and combinations thereof. The memory 204 may be either volatile or nonvolatile memory and may include RAM, flash, cache, disk drives, and other computer readable memory storage devices. Although shown as a single entity, the memory 204 may be divided into different memory storage elements such as RAM and one or more hard disk drives. In certain embodiments, the memory 204 includes various instructions that are executable by the processor 202 to perform one or more techniques described herein. Here, the memory 204 may include the detection component 145, the prevention component 155, the equipment control tool 125, or a combination thereof.

The storage 206 may be a combination of fixed and/or removable storage devices, such as fixed disc drives, removable memory cards, optical storage, network attached storage (NAS), or a storage area-network (SAN). In certain embodiments, the storage 206 may include seizure trigger information 208 and video 226.

Note that FIG. 2 illustrates a reference example configuration of a computing environment 200 in which the techniques presented herein can be implemented and that other configurations of the computing environment 200 consistent with the functionality described herein are contemplated. For example, although FIG. 2 depicts a detection component 145, a prevention component 155, and an equipment control tool 125, in certain embodiments, one or more of these components may be integrated in a single component or distributed across multiple computing devices.

Figure 3:
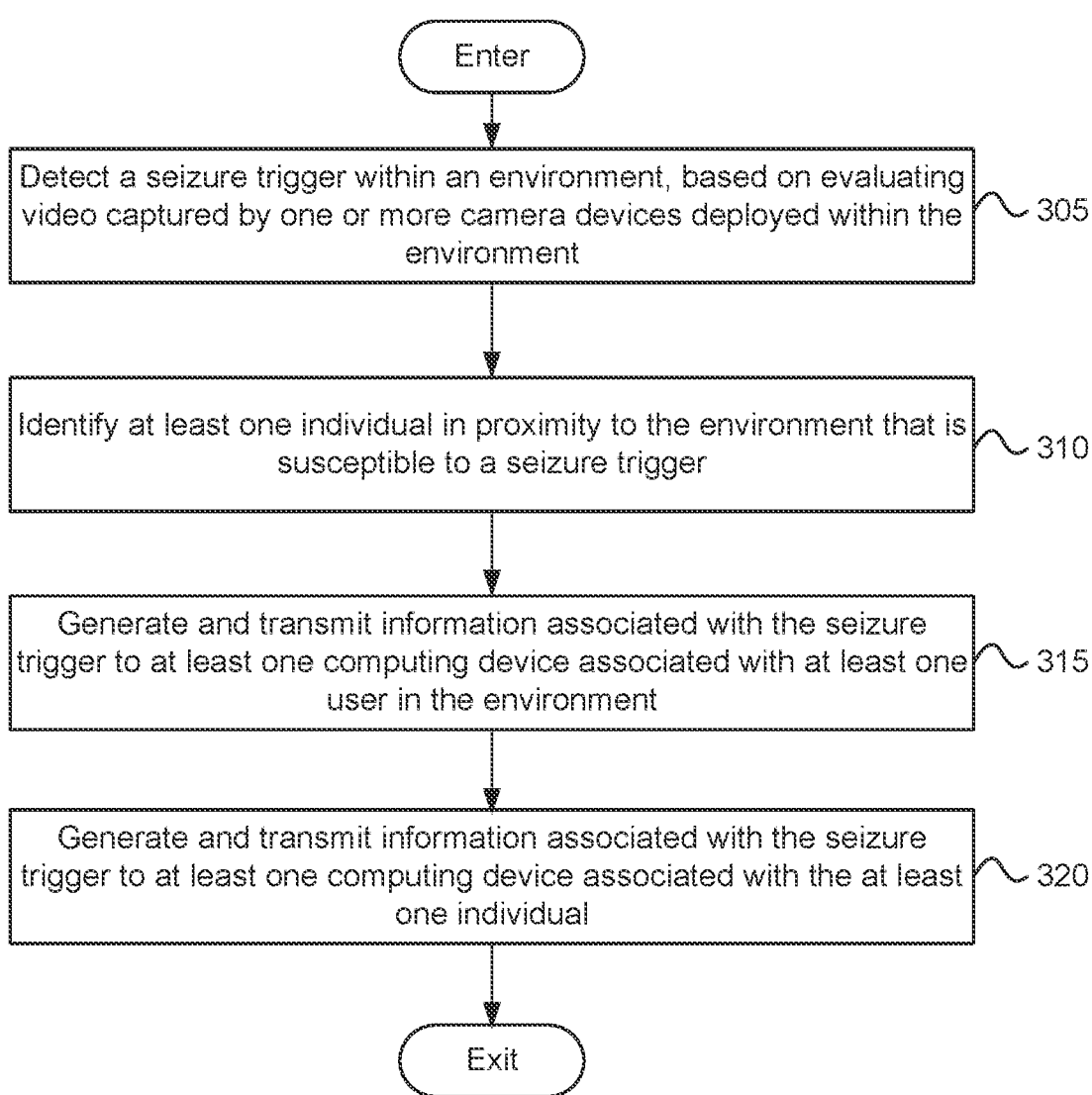
FIG. 3 is a flowchart of an example method for preventing seizure activity in an environment, according to one embodiment.

FIG. 3 is a flowchart of a method 300 for preventing seizure activity in an environment, according to one embodiment. Method 300 may be performed by a computing device, such as camera device 140 or computing system 120.

Method 300 enters at block 305, where the computing device detects a seizure trigger within an environment (e.g., environment 110), based on video captured by one or more camera devices (e.g., camera devices 140) deployed within the environment. As noted, the computing device may evaluate the video using one or more computer vision algorithms configured to detect seizure triggers in order to determine whether a seizure trigger is present within the environment. The seizure trigger may be a particular light pattern (e.g., certain frequencies and/or color/contrast changes) that is associated with causing onset of seizure activity in sensitive individuals, such as individuals with epilepsy.

At block 310, the computing device identifies at least one individual (e.g., user 105) in proximity to the environment that is susceptible to the seizure trigger. For example, the computing device may identify the at least one individual based on interacting with a computing device associated with the at least one individual. As noted, such a computing device may host an application associated with the environment that stores information within a user profile indicating that the at least one individual is susceptible to seizure triggers. Such an application may also indicate when the at least one individual is in proximity (e.g., within a threshold distance) to the environment and/or to the seizure trigger detected within the environment.

In another embodiment, the computing device may identify the at least one individual based on interacting with (i) another computing device associated with a user in the environment responsible for managing the environment (e.g., store personnel), (ii) a computing system associated with the environment, or (iii) a combination thereof. For example, the computing device may receive an indication from the other computing device and/or the computing system that the at least one individual is in proximity to the environment and/or to the seizure trigger and that the at least one individual is susceptible to seizure triggers.

At block 315, the computing device generates and transmits information associated with the seizure trigger to at least one computing device (e.g., computing device 170) associated with at least one user (e.g., user 175). The information may include, for example, a location of the seizure trigger within the environment, a type of the seizure trigger, or a combination thereof.

At block 320, the computing device generates and transmits information associated with the seizure trigger to at least one computing device (e.g., computing device 160) associated with the at least one individual (e.g., user 105). The information may include, for example, a location of the seizure trigger within the environment, a type of the seizure trigger, or a combination thereof.

In certain embodiments, the method 300 may further include, transmitting, by the computing device, an indication that the seizure trigger is no longer present to at least one of the at least one individual or the user, after detecting that the seizure trigger is no longer present within the environment.

Figure 4:
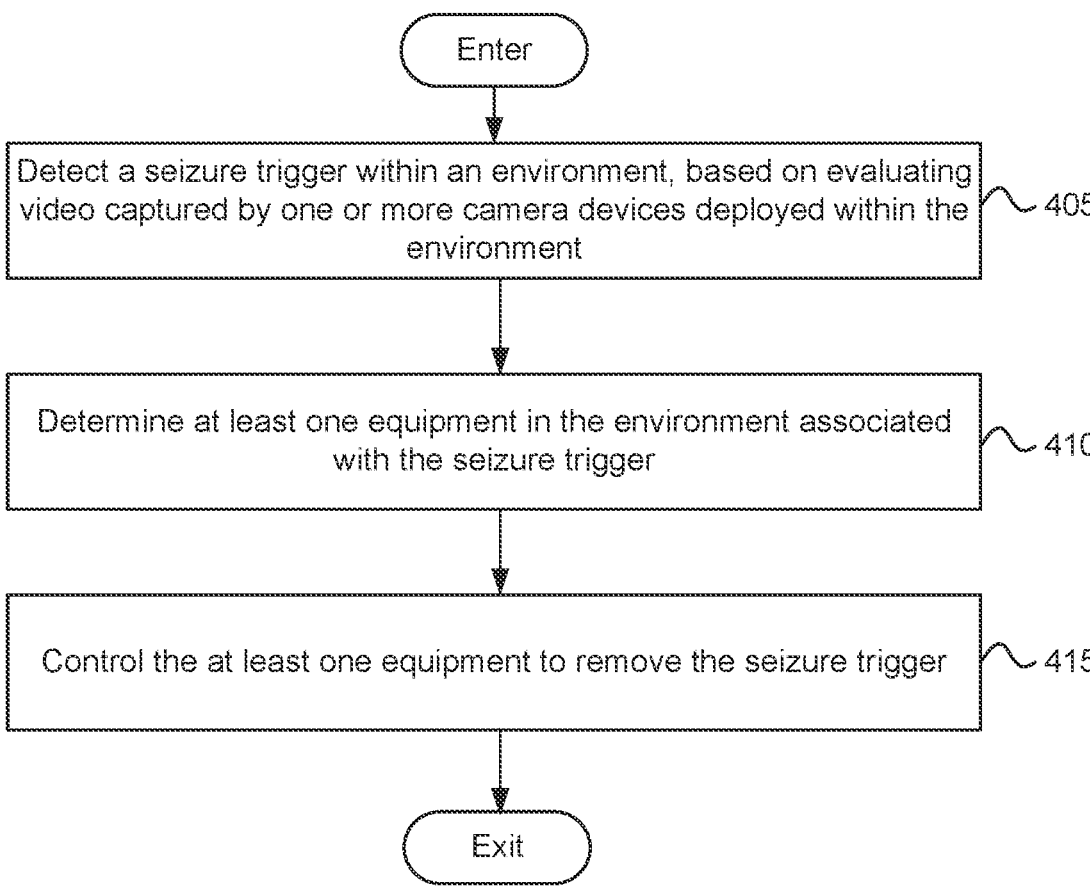
FIG. 4 is a flowchart of another example method for preventing seizure activity in an environment, according to one embodiment.

FIG. 4 is a flowchart of a method 400 for preventing seizure activity in an environment, according to one embodiment. Method 400 may be performed by a computing device, such as camera device 140, computing system 120, or a combination thereof.

Method 400 may enter at block 405, where the computing device detects a seizure trigger within an environment (e.g., environment 110), based on video captured by one or more camera devices (e.g., camera devices 140) deployed within the environment. As noted, the computing device may evaluate the video using one or more computer vision algorithms configured to detect seizure triggers in order to determine whether a seizure trigger is present within the environment. The seizure trigger may be a particular light pattern (e.g., certain frequencies and/or color/contrast changes) that is associated with causing onset of seizure activity in sensitive individuals, such as individuals with epilepsy.

At block 410, the computing device determines at least one equipment in the environment associated with the seizure trigger. For example, the computing device may determine that the seizure trigger is occurring from a set of lighting devices in a light fixture, on a display, television, POS device, etc.

At block 415, the computing device controls the at least one equipment to remove the seizure trigger. For example, the computing device may interact with an equipment control tool (e.g., equipment control tool 125) to send commands to the at least one equipment to turn off the set of lighting devices associated with the seizure trigger and/or modify behavior of the set of lighting devices associated with the seizure trigger.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to present disclosure shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access applications (e.g., detection component 145, prevention component 155, and equipment control tool 125) or related data available in the cloud. For example, the detection component 145, prevention component 155, and/or equipment control tool 125 could execute on a computing system in the cloud and perform one or more techniques described herein to prevent (or at least mitigate) the occurrence of seizure activity in the environment, and store information associated with seizure triggers detected in the environment at a storage location in the cloud. Doing so allows a user to access this information from any computing system attached to a network connected to the cloud (e.g., the Internet).

While the foregoing is directed to embodiments of the present disclosure, other and further embodiments of the disclosure may be devised without departing from the basic scope thereof, and the scope thereof is determined by the claims that follow.

What is claimed is:

1. A computer-implemented method comprising:

detecting a seizure trigger emitting within an environment via one or more camera devices deployed in the environment, wherein detecting the seizure trigger comprises:

receiving, by the one or more camera devices, image data emitted from a display device within the environment, wherein the image data comprises a light pattern projected from the display device, and evaluating the light pattern using a computer vision algorithm to determine a light pattern flicker rate and a high contrast light transition;

determining a user is within a predetermined proximity from the detected seizure trigger within the environment; and responsive to determining that the user is within the predetermined proximity from the detected seizure trigger;

adjusting the light pattern flicker rate to a static light pattern non-flicker rate, and causing the display device to deactivate the high contrast light transition emitting from the display device.

2. The computer-implemented method of claim 1, wherein:

the seizure trigger is detected within a first region of a plurality of regions within the environment.

3. The computer-implemented method of claim 1, wherein determining the user is within the predetermined proximity from the detected seizure trigger comprises:

receiving an indication from a computing device associated with the user that the user is located within a threshold distance of a region in the environment in which the seizure trigger is detected; and receiving an indication from the computing device that the user is susceptible to the seizure trigger.

4. The computer-implemented method of claim 1, wherein determining the user is within the predetermined proximity from the detected seizure trigger comprises receiving an indication from a computing system associated with the environment that the user is located in the environment and that the user is susceptible to the seizure trigger.

5. The computer-implemented method of claim 1, further comprising after detecting that the seizure trigger is no longer present within the environment, transmitting an indication that the seizure trigger is no longer present to a computing device associated with the user.

6. A computing system comprising:

one or more memories collectively storing computer-executable instructions; and one or more processors communicatively coupled to the one or more memories, the one or more processors being collectively configured to execute the computer-executable instructions to cause the computing system to perform an operation comprising:

detecting a seizure trigger emitting within an environment via one or more camera devices deployed in the environment, wherein detecting the seizure trigger comprises:

receiving, by one or more camera devices, image data emitted from a display device within the environment, wherein the image data comprises a light pattern projected from the display device, and evaluating the light pattern using a computer vision algorithm to determine a light pattern flicker rate and a high contrast light transition;

determining that a user is within a predetermined proximity from the detected seizure trigger within the environment; and responsive to determining that the user is within the predetermined proximity from the detected seizure trigger;

adjusting the light pattern flicker rate to a static light pattern non-flicker rate, and causing the display device to deactivate the high contrast light transition emitting from the display device.

7. The computing system of claim 6, wherein:

the seizure trigger is detected within a first region of a plurality of regions within the environment.

8. The computing system of claim 6, wherein determining the user comprises:

receiving an indication from a computing device associated with the user that the user is located within a threshold distance of a region in the environment in which the seizure trigger is detected; and receiving an indication from the computing device that the user is susceptible to the seizure trigger.

9. The computing system of claim 6, wherein determining the user is within the predetermined proximity from the detected seizure trigger comprises receiving an indication from another computing system associated with the environment that the user is located in the environment and that the user is susceptible to the seizure trigger.

10. The computing system of claim 6, further comprising after detecting that the seizure trigger is no longer present within the environment, transmitting an indication that the seizure trigger is no longer present to a computing device associated with the user.

11. A non-transitory computer-readable medium comprising computer-executable instructions, which when collectively executed by one or more processors of a computing system cause the computing system to perform an operation comprising:

detecting a seizure trigger emitting within an environment via one or more camera devices deployed in the environment, wherein detecting the seizure trigger comprises:

receiving, by the one or more camera devices, image data emitted from a display device within the environment, wherein the image data comprises a light pattern projected from the display device, and evaluating the light data using a computer vision algorithm to determine a light pattern flicker rate and a high contrast light transition;

determining that a user is within a predetermined proximity from the detected seizure trigger within the environment; and responsive to determining that the user is within the predetermined proximity from the detected seizure trigger;

adjusting the light pattern flicker rate to a static light pattern non-flicker rate, and causing the display device to deactivate the high contrast light transition emitting from the display device.

12. The non-transitory computer-readable medium of claim 11, wherein:

the seizure trigger is detected within a first region of a plurality of regions within the environment.

13. The non-transitory computer-readable medium of claim 11, further comprising after detecting that the seizure trigger is no longer present within the environment, transmitting an indication that the seizure trigger is no longer present to a computing device associated with the user.

* * * * *